United States Patent [19]

Yoshikawa et al.

[11] 4,349,509
[45] Sep. 14, 1982

[54] OXYGEN INDICATOR ADAPTED FOR PRINTING OR COATING AND OXYGEN-INDICATING DEVICE

[75] Inventors: Yoshio Yoshikawa; Takanari Nawata, both of Tokyo; Mikio Goto, Matsudo; Yukio Kondo, Yono, all of Japan

[73] Assignee: Mitsubishi Gas Chemical Co., Inc., Tokyo, Japan

[21] Appl. No.: 163,870

[22] Filed: Jun. 27, 1980

[30] Foreign Application Priority Data

Jul. 3, 1979 [JP] Japan .................................. 54-84122

[51] Int. Cl.³ .................... G01N 31/22; C09K 3/00
[52] U.S. Cl. .................................... 422/57; 23/932; 252/408; 422/56; 426/87
[58] Field of Search .................... 252/408; 422/56, 57; 23/932; 426/87

[56] References Cited

U.S. PATENT DOCUMENTS 3,963,442 6/1976 Bullard et al. ...................... 252/408
4,169,811 10/1979 Yoshikawa et al. ................ 252/408

FOREIGN PATENT DOCUMENTS 54-48294 4/1979 Japan ..................................... 23/932
54-138489 10/1979 Japan ................................. 252/408
55-43428 3/1980 Japan ..................................... 23/932

*Primary Examiner*—Joseph E. Evans
*Attorney, Agent, or Firm*—Frishauf, Holtz, Goodman & Woodward

[57] ABSTRACT

An oxygen indicator adapted for printing or coating which comprises (a) at least one reducing agent, (b) a dyestuff causing color change when it is reduced with the reducing agent, (c) at least one thickening agent and (d) at least one solvent and a sheet-like oxygen indicator in which a composition comprising the above four components (a)-(d) is coated or printed on a substrate are disclosed.

21 Claims, No Drawings

OXYGEN INDICATOR ADAPTED FOR PRINTING OR COATING AND OXYGEN-INDICATING DEVICE

BACKGROUND OF THE INVENTION

This invention relates to an oxygen indicator adapted for printing and also relates to a sheet-like oxygen indicator.

The color of an oxygen indicator changes from one color in an aerobic atmosphere to a different color in an anaerobic atmosphere. So, whether oxygen is present or not in the atmosphere in which the indicator is placed is easily determined by its color.

An oxygen indicator comprising an aqueous solution of sodium hydroxide, glucose and Methylene Blue has been known.

Recently, oxygen-free packaging of foodstuff, e.g. vacuum-packed package, package containing an oxygen absorbent, nitrogen filled package, and so on, have been widely demanded in order to prolong the shelf-life of the foodstuff. A convenient oxygen indicator which has high sensitivity and long life is necessary for the control of such packing systems. However, the shelf-life of the prior art oxygen indicators is too short for such a purpose.

Some of the present inventors have proposed an oxygen indicator in a powder state or a tablet state. Such oxygen indicator is disclosed in U.S. Pat. No. 4,169,811 by Yoshio Yoshikawa et al. patented on Oct. 2, 1979 which is incorporated herein as reference.

SUMMARY OF THE INVENTION

The present inventors carried out research on an oxygen indicator adapted for printing or coating on a substrate, such as cellulosic sheet or plastic sheet. As a result, we found that a composition comprising a reducing agent, a dyestuff, a thickening agent and a solvent is suitable for printing or coating on a substrate.

An object of this invention is to provide an oxygen indicator suitable for printing or coating on a substrate.

Another object of this invention is to provide an oxygen-indicating device comprising a substrate having the oxygen indicator supported thereon.

DESCRIPTION OF THE PREFERRED EMBODIMENT

This invention relates to an oxygen indicator suitable for printing which comprises (a) at least one reducing agent, (b) a dyestuff causing color change when it is reduced with the reducing agent, (c) at least one thickening agent and (d) at least one solvent.

This invention relates to an oxygen-indicating device comprising a substrate and a composition coated or printed thereon which comprises (a) at least one reducing agent, (b) a dyestuff causing color change when it is reduced with the reducing agent, (c) at least one thickening agent and (d) at least one solvent.

Examples of the reducing agents include mixtures of at least one alkaline substance and dithionites, ferrous compounds, reducing saccharides or mixture thereof; ascorbic acid; erysorbic acid or salt thereof; stannous salts; hydroxyamine; hydrazine; keto-carbonxylic acids; sulfoxylates; alkali metal sulfides and boron hydrides.

Of the reducing agents, mixtures of at least one alkaline substance and a dithionite, a ferrous compound or a reducing saccharide are preferred.

Dithionite means a compound represented by the formula $$M_xS_2O_4$$

wherein M is monovalent or divalent cationic atom, or monovalent or divalent cationic atomic group; when M is monovalent, x is 2, and when M is divalent, x is 1. In general, it is called hydrosulfite. Sodium dithionite and zinc dithionite are the preferred dithionites. Sodium dithionite is most preferred.

The ferrous compounds employed in the present invention include both inorganic salts such as ferrous sulfate, ferrous chloride or ferrous ammonium sulfate and organic salts, such as ferrous oxalate or ferrous lactate and iron sulfide. The inorganic salts, such as ferrous sulfate, ferrous chloride and ferrous ammonium sulfate are preferred from the view points of easy handling availability and function of the oxygen indicator.

Reducing saccharides include, for example monosaccharides, such as mannose, glucose, fructose, erythrose, and araginose; and reducing oligosaccharides, such as maltose and lactose. Glucose, fructose and maltose are preferred from view points of easy handling, and availability.

The alkaline materials used with the dithionites, the reducing saccharides or the ferrous compound include hydroxides or weak acid salts of alkali metals or alkaline earth metals, such as $K_2HPO_4$, $Na_2HPO_4$, $K_3PO_4$, $Na_3PO_4$, $K_2CO_3$, $Na_2CO_3$, $MgCO_3$, $CaCO_3$, $Mg(OH)_2$, $Ca(OH)_2$, NaOH and KOH. Mixtures of two or more alkaline substances may be used.

The dyestuff employed in the practice of this invention is selected from the group consisting of compounds represented by the formula $$\left[ \begin{array}{c} R_5 \diagdown \underset{R_9}{\overset{R_6}{\diagup}} \diagup \underset{R_{10}}{\overset{N}{\diagdown}} \diagup \underset{R_4}{\diagdown} Y^+ \diagup \underset{R_3}{\diagdown} \diagup \underset{R_8}{\overset{R_1}{\diagup}} \underset{R_7}{\diagdown} \end{array} \right] X^- \quad (I)$$

wherein $-Y^+=$ is selected from $-O^+=$, $-S^+=$ or $$\overset{\diagdown}{\underset{\diagup}{N^+}} -Z$$

wherein Z is selected from hydrogen, alkyl group having 1-4 carbon atoms or aryl group having 6-7 carbon atoms; each of $R_1-R_6$ is independently selected from hydrogen, alkyl group having 1-4 carbon atoms or nitro group; each of $R_7-R_{10}$ is independently selected from hydrogen, or alkyl group having 1-4 carbon atoms; and X is halogen; compounds represented by the formula (II)

$MO_3S$ — [benzothiazole-C=C-benzothiazole] — $SO_3M$ wherein M is alkali metal.

Examples of the dyestuffs include Methylene Blue (C.I. Basic Blue 9), New Methylene Blue (C.I. Basic Blue 24), C.I. Basic Blue 3, phenosafranine, Capri Blue, Lauth's Violet, Methylene Green (C.I. Basic Green 5), Neutral Red, Safranine T (C.I. Basic Red 2), Indigo Carmine, Setoglaucine, Reactive Blue 19, Xylene Cyanol, Riboflavin, Erythrosine, Xylene Blue, Fast Green, Vad Green 1, Acid Blue 59 and Acid Red 51.

The thickening agent of this invention serves to prevent the oxygen indicator from running, when it is printed or coated on the substrate. The thickening agents employed in the practice of this invention are water-soluble polymeric substances. Examples of the water-soluble polymeric substances include sodium carboxymethyl cellulose, hydroxyethyl cellulose, methylcellulose, sodium alginate, polyvinyl alcohol, gum arabic powder, gumtragacanth, dextrin and casein. The amount of the thickening agent employed is in the range of from 0.05 to 10% by weight on the basis of weight of the total composition, preferably in the range of 0.1–5% by weight.

The solvents used in the practice of this invention include water and/or alcohols, such as methyl alcohol, ethyl alcohol or isopropyl alcohol and mixtures thereof. Mixtures of water and/or an alcohol and other solvent may be used as a solvent.

The oxygen indicator of this invention may be used as a flexographic, gravure printing or letter press printing ink. In this case, the oxygen indicator may contain other components, such as binder, resin, etc. which are conventionally used in these inks.

The oxygen indicator can be prepared by blending (a) at least one reducing agent, (b) a dyestuff causing color change when it is reduced with the reducing agent, (c) at least one thickening agent and (d) at least one solvent. If there is a possibility of these components clumping when they are blended, at least one surfactant may be added to the oxygen indicator in order to prevent such clumping. Addition of a surfactant to the oxygen indicator also improves its storage stability.

The surfactant is selected from the group consisting of alkylsulfates, alkylnaphthalenesulfonates, naphthalenesulfonic acid-formalin condensates, polyoxyethylene alkylsulfates, polyoxyethylenealkylether, polyoxyethylene alkylphenolethers, polyoxyethylene fatty acid esters, polyoxyethylene sorbitan fatty acid esters, polyoxyethylene alkylamines, alkylamino acids, quaternary ammonium salts and mixtures thereof.

The surfactant may be used in amount of 0.01 to 10% by weight on the basis of weight of total composition, preferably 0.05–5% by weight.

When aggregation can be not completely prevented, even with the addition of a surfactant to the system, a neutral or alkaline compound which is slightly soluble in water, may be added to the system. The use of a compound which is slightly soluble in water prevents color shading, provides uniform coloration and improves storage stability of the oxygen indicator and life of the printed substance. Examples of such compounds include $BaSO_4$, $CaCO_3$, $MgCO_3$, $Mg(OH)_2$, $Ca(OH)_2$ and the like. The amount of the compound employed is in the range of from 2–70% by weight on the basis of total composition, preferably in the range of from 5–50% by weight.

When a dyestuff which is somewhat unstable to a strong alkaline substance is to be used with a strong alkaline substance, the strong alkaline substance is previously adsorbed into paper or cloth and then a solution containing a reducing substance and the dyestuff is coated or printed on the paper or the cloth.

An inert dyestuff not causing color change through reaction with other components in the indicator may be added to the system to give a desired color.

Substrates satisfactory for supporting the oxygen indicator include cellulosic substrates and plastic substrates. Cellulosic substrates are preferred, because the present oxygen indicator is easily printed or coated thereon. The substrate may be laminated. The oxygen indicator-printed or coated substrate may be fabricated into a bag.

In use, the present oxygen-indicating device is placed in the package containing the things to be preserved. When the present oxygen-indicating device is employed in the vacuum pack method, nitrogen-filled method or oxygen absorption method for preserving fresh or processed foodstuffs or preventing oxidation of organic chemicals or metals, the presence or absence of oxygen in the sealed container can be detected. Incomplete removal of gas and leakage of air due to incomplete sealing can easily be observed by using the present oxygen indicating device.

The present oxygen indicator may be used in place of part of the ink constituting package design on a packaging film.

The present invention is further illustrated by the following non-limiting Examples. The percent and part are by weight, unless otherwise specified.

EXAMPLE 1

A solution was prepared by blending 4.2 parts of a 10% solution of glucose, 0.1 part of 1 N sodium hydroxide solution and 0.1 part of Methylene Blue (50 mg of Methylene Blue in 30 ml of water) and, 0.05 g of sodium carboxymethyl cellulose per 10 ml of the total solution. When a picture was drawn on a filter paper with the solution, the oxygen indicator did not run on the paper.

When the resulting blue paper was allowed to stand in a nitrogen atmosphere (oxygen concentration therein was 0.1%) for several hours, it turned colorless. When oxygen was added to the atmosphere, it turned blue again.

For comparison, when the solution comprising glucose, sodium hydroxide and Methylene blue was prepared. When a picture was drawn on a filter paper with the solution, the oxygen indicator ran on the paper.

EXAMPLES 2–7

The procedure of Example 1 was repeated except that reducing agents, alkaline substances, dyestuffs and thickening agent as given in the following Table 1 are used in amount as given in Table 1. When a picture was drawn on a filter paper with each of the solution, the oxygen indicator did not run on the paper. The color of the oxygen indicator-coated paper under aerobic condition or anaerobic conditions is shown in Table 1.

TABLE 1

| Ex. No. | Reducing agent Composition | Reducing agent Amount (parts) | Alkaline substance Composition | Alkaline substance Amount (parts) | Dyestuff Composition | Dyestuff Amount (parts) | Thickening Agent Compound | Thickening Agent Amount of agent per 10 ml of total solution (gr) | Color of oxygen indicator-coated paper under aerobic conditions | Color of oxygen indicator-coated paper under anaerobic conditions |
|---|---|---|---|---|---|---|---|---|---|---|
| 2 | 10% glucose | 4.2 | 1N—NaOH | 0.1 | 50 mg of Indigo Carmine in 30 ml of water | 0.1 | CMC—Na* | 0.05 | blue | yellow |
| 3 | 10% glucose in 50% ethyl alcohol solution | 4.2 | 1N—KOH in 50% ethanol solution | 0.1 | 50 mg of Methylene Blue in 30 ml of 50% ethanol solution | 0.1 | methyl cellulose | 0.05 | blue | white |
| 4 | 10% sodium hydrosulfite | 4.2 | 1N—NaOH | 0.1 | 50 mg of Methylene Blue in 30 ml of water | 0.1 | sodium alginate | 0.05 | blue | white |
| 5 | 10% FeSO$_4$ | 4.2 | " | 0.1 | 50 mg of Methylene Blue in 30 ml of water | 0.1 | polyvinyl alcohol | 0.05 | blue | white |
| 6 | 5% sodium ascorbate | 4.2 | — | | 50 mg of Methylene Blue in 30 ml of water | 0.1 | CMC—Na | 0.05 | light blue | white |
| 7 | 5% SnCl$_2$ | 4.2 | — | | 50 mg of Methylene Blue in 30 ml of water | 0.1 | " | 0.05 | light blue | white |

*CMC—Na is sodium carboxymethyl cellulose.

EXAMPLE 8

An oxygen indicator solution was prepared by incorporating 50 mg of Methylene Blue, 5 g of D-glucose, 0.2 g of K$_3$PO$_4$ and 0.2 g of sodium alginate and 0.2 g of naphthalene sulfonic acid-formalin condensate in 50 ml of water. 5 g Of light calcium carbonate and 20 mg of Acid Red were added to the solution to form a uniform solution. A letter was drawn on a paper with the solution. When the resulting blue paper was allowed to stand in a nitrogen atmosphere (oxygen concentration therein was 0.1%) for 20 hours, it turned pink. When oxygen was added to the atmosphere, it turned blue.

What is claimed is:

1. An oxygen indicator adapted for printing which comprises
   (a) at least one reducing agent selected from the group consisting of mixtures of at least one alkaline substance and dithionites, ferrous compounds, reducing saccharides or mixtures thereof; ascorbic acid; erysorbic acid or a salt thereof; stannous salts; hydroxyamine; hydrazine; keto-carboxylic acids; sulfoxylates; alkali metal sulfides and boron hydrides;
   (b) a dyestuff which has a color in an atmosphere containing oxygen and a different color in a non-oxygen containing atmosphere when it is reduced with said reducing agent;
   (c) at least one thickening agent selected from the group consisting of sodium carboxymethyl cellulose, hydroxyethyl cellulose, methyl-cellulose, sodium alginate, polyvinyl alcohol, gum arabic powder, gum tragacanth, dextrin and casein in an amount of 0.05–10% by weight on the basis of (a), (b), (c) and (d); and
   (d) at least one solvent selected from the group consisting of water, alcohols, and mixtures thereof.

2. A sheet-like oxygen indicator comprising a sheet selected from the group consisting of cellulosic sheets and plastic sheets and a composition coated or printed thereon which comprises
   (a) at least one reducing agent selected from the group consisting of mixtures of at least one alkaline substance and dithionites, ferrous compounds, reducing saccharides or mixtures thereof; ascorbic acid; erysorbic acid or a salt thereof; stannous salts; hydroxyamine, hydrazine; keto-carboxylic acids; sulfoxylates; alkali metal sulfides and boron hydrides;
   (b) a dyestuff which has a color in an atmosphere containing oxygen and a different color in a non-oxygen containing atmosphere when it is reduced with said reducing agent;
   (c) at least one water soluble polymeric compound in an amount of 0.05 to 10% by weight on the basis of weight of the total composition selected from the group consisting of sodium carboxymethyl cellulose, hydroxyethyl cellulose, methyl cellulose, sodium alginate, polyvinyl alcohol, gum arabic powder, gum tragacanth, dextrin and casein; and
   (d) at least one solvent selected from the group consisting of water, alcohols, and mixtures thereof.

3. The oxygen indicator as defined in claim 1 wherein the reducing agent is selected from mixtures of at least one alkaline substance and dithionites, ferrous compounds, reducing saccharides and mixtures thereof.

4. The oxygen indicator as defined in claim 3 wherein the alkaline substance is selected from hydroxides or weak acid salts of alkali metals or alkaline earth metals.

5. The oxygen indicator as defined in claim 1 wherein the dyestuff is represented by the formula

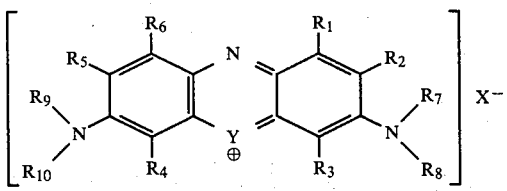

wherein $-Y^+=$ is selected from the group consisting of $-O+=$, $-S+=$ and

wherein Z is selected from the group consisting of hydrogen, an alkyl group having 1-4 carbon atoms and an aryl group having 6-7 carbon atoms; each of $R_1$-$R_6$ is independently selected from the group consisting of hydrogen, an alkyl group having 1-4 carbon atoms, an alkoxy group having 1-4 carbon atoms and a nitro group; each of $R_7$-$R_{10}$ is independently selected from the group consisting of hydrogen and an alkyl group having 1-4 carbon atoms; and X is halogen.

6. The oxygen indicator as defined in claim 1 wherein the dyestuff is represented by the formula

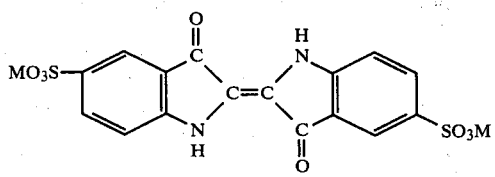

wherein M is an alkali metal.

7. The oxygen indicator as defined in claim 1, characterized in that it further contains at least one surfactant.

8. The oxygen indicator as defined in claim 7 wherein the surfactant is selected from the group consisting of alkylsulfates, alkylnaphthalenesulfonates, naphthalenesulfonic acid-formalin condensates, polyoxyethylene alkylsulfates, polyoxyethylenealkylether, polyoxyethylene alkylphenolethers, polyoxyethylene fatty acid esters, polyoxyethylene sorbitan fatty acid esters, polyoxyethylene alkylamines, alkylamino acid, quaternary ammonium salts and mixtures thereof.

9. The oxygen indicator as defined in claim 1, characterized in that it further contains at least one neutral or alkaline compound which is slightly soluble in water.

10. The oxygen indicator as defined in claim 9 wherein the compound which is slightly soluble in water is selected from the group consisting of $BaSO_4$, $CaCO_3$, $MgCO_3$, $Mg(OH)_2$ and $Ca(OH)_2$.

11. The oxygen indicator as defined in claim 1, characterized in that it further contains an inert dyestuff not causing color change through reacting with other components in the indicator.

12. The sheet like oxygen indicator as defined in claim 2 wherein the reducing agent is selected from mixtures of at least one alkaline substances and dithionites, ferrous compounds, reducing saccharides or mixtures thereof.

13. The sheet like oxygen indicator as defined in claim 12 wherein the alkaline substance is selected from hydroxides or weak acid salts of alkali metals or alkaline earth metals.

14. The sheet like oxygen indicator as defined in claim 12 or 13, characterized by adsorbing or adhering the alkaline substance onto or to the sheet, and then printing or coating the dyestuff, dithionites, reducing saccharides or ferrous compounds and solvent.

15. The sheet like oxygen indicator as defined in claim 2 wherein the dyestuff is represented by the formula

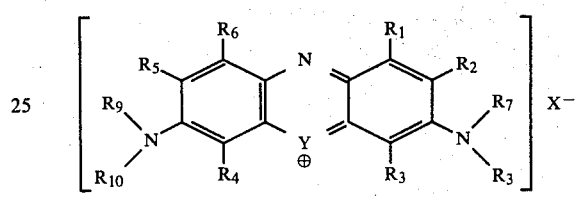

wherein $-Y^{30}=$ is selected from the group consisting of $-O^+=$, $-S^+=$ and

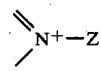

wherein Z is selected from the group consisting of hydrogen, an alkyl group having 1-4 carbon atoms and an aryl group having 6-7 carbon atoms; each of $R_1$-$R_6$ is independently selected from the group consisting of hydrogen, an alkyl group having 1-4 carbon atoms, an alkoxy group having 1-4 carbon atoms and a nitro group; each of $R_7$-$R_{10}$ is independently selected from the group consisting of hydrogen and an alkyl group having 1-4 carbon atoms; and X is halogen.

16. The sheet like oxygen indicator as defined in claim 2 wherein the dyestuff is the one represented by the formula

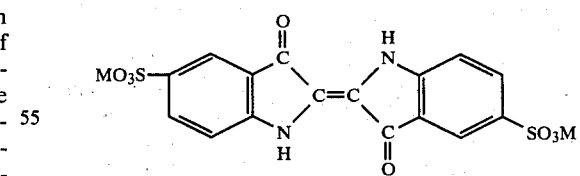

wherein M is alkali metal.

17. The sheet like oxygen indicator as defined in claim 2, characterized in that it further contains at least one surfactant.

18. The sheet like indicator as defined in claim 17 wherein the surfactant is selected from the group consisting of alkylsulfates, alkylnaphthalenesulfonates, naphthalenesulfonic acid-formalin condensates, polyoxyethylene alkylsulfates, polyoxyethylenealkylether, polyoxyethylene alkylphenolethers, polyoxyethylene fatty acid esters, polyoxyethylene sorbitan fatty acid esters, polyoxyethylene alkylamines, alkylamino acid, quaternary ammonium salts and mixtures thereof.

19. The sheet like oxygen indicator as defined in claim 2 characterized in that it further contains at least one neutral or alkaline compound which is slight soluble in water.

20. The sheet like oxygen indicator as defined in claim 19 wherein the compound which is slightly soluble in water is selected from the group consisting of $BaSO_4$, $CaCO_3$, $MgCO_3$, $Mg(OH)_2$ and $Ca(OH)_2$.

21. The sheet like oxygen indicator as defined in claim 2, characterized in that it further contains an inert dyestuff which does not cause color change through reaction with other components in the indicator.

* * * * *

UNITED STATES PATENT AND TRADEMARK OFFICE
CERTIFICATE OF CORRECTION

PATENT NO. : 4,349,509

DATED : September 14, 1982

INVENTOR(S) : Yoshio YOSHIKAWA et al

It is certified that error appears in the above-identified patent and that said Letters Patent is hereby corrected as shown below:

Column 2, lines 61-67, in the lower portion of the formula, replace "$\overset{\|}{C}$" with -- $\overset{\|}{O}$ --.

Column 8, lines 22-28, in the lower right portion of the formula, replace "$R_3$" with --$R_8$--.

Column 8, line 30, replace "$-Y^{30}=$" with -- $-Y^{+}=$ --.

Signed and Sealed this

Tenth Day of April 1984

[SEAL]

*Attest:*

GERALD J. MOSSINGHOFF

*Attesting Officer*  *Commissioner of Patents and Trademarks*